(12) United States Patent
Aburada

(10) Patent No.: US 11,517,424 B2
(45) Date of Patent: Dec. 6, 2022

(54) TOOL FOR MOLDING DYSPHONIA TREATMENT TOOL, AND METHOD FOR BENDING FRONT PIECE OF DYSPHONIA TREATMENT TOOL

(71) Applicant: NOBELPHARMA CO., LTD., Tokyo (JP)

(72) Inventor: Takako Aburada, Tokyo (JP)

(73) Assignee: Nobelpharma Co., Ltd., Tokyo (JP)

( * ) Notice: Subject to any disclaimer, the term of this patent is extended or adjusted under 35 U.S.C. 154(b) by 461 days.

(21) Appl. No.: 16/622,710

(22) PCT Filed: Jun. 13, 2018

(86) PCT No.: PCT/JP2018/022611
§ 371 (c)(1),
(2) Date: Jun. 29, 2020

(87) PCT Pub. No.: WO2018/230613
PCT Pub. Date: Dec. 20, 2018

(65) Prior Publication Data
US 2020/0330219 A1 Oct. 22, 2020

(30) Foreign Application Priority Data
Jun. 14, 2017 (JP) .............................. JP2017-117033

(51) Int. Cl.
*A61F 2/20* (2006.01)
(52) U.S. Cl.
CPC ........ *A61F 2/20* (2013.01); *A61F 2220/0008* (2013.01); *A61F 2240/001* (2013.01)
(58) Field of Classification Search
CPC ................ A61F 2/20; A61F 2220/0008; A61F 2240/001; A61F 2220/0033;
(Continued)

(56) References Cited

U.S. PATENT DOCUMENTS

2004/0254642 A1* 12/2004 Isshiki ...................... A61F 2/20
623/9

FOREIGN PATENT DOCUMENTS

JP  2003-102743  4/2003
JP  2005-000330  1/2005
(Continued)

OTHER PUBLICATIONS

International Search Report issued in International Application No. PCT/JP2018/022611, dated Oct. 16, 2018, 4 pages.
(Continued)

*Primary Examiner* — Jennifer Dieterle
*Assistant Examiner* — Rebecca Lynee Zimmerman
(74) *Attorney, Agent, or Firm* — Hamre, Schumann, Mueller & Larson, P.C.

(57) ABSTRACT

The present invention provides a jig for forming a dysphonia treatment tool, the jig being capable of bending a front piece in a position not through a hole. A jig 20C for forming a dysphonia treatment tool X by deformation, the dysphonia treatment tool X including: a plurality of clamping sections each having a front piece 1a disposed on a front surface of incised thyroid cartilage and a rear piece disposed on a rear surface of the thyroid cartilage, the clamping sections configured to be fit to respective cut ends of the thyroid cartilage facing each other; and a bridging section linking the clamping sections to each other, the front piece having a hole 3 formed therein, the forming jig includes a clip section 22 having a pair of maintaining sections 21a, 21b configured to sandwich the front piece 1a from both surfaces to cover at least a portion of the hole 3.

15 Claims, 11 Drawing Sheets

(58) Field of Classification Search
CPC ............... A61F 2/30756; A61F 2/0036; A61F 2/30749; A61B 17/24
See application file for complete search history.

(56) References Cited

FOREIGN PATENT DOCUMENTS

| | | |
|---|---|---|
| JP | 2010-051381 | 3/2010 |
| JP | 2017-118920 | 7/2017 |
| WO | 98/29058 | 7/1998 |
| WO | 2013/172940 | 11/2013 |

OTHER PUBLICATIONS

Sanuki, et al., Surgical treatment for adductor spasmodic dysohonia, Otologia Fukuoka, vol. 2005, No. 51, No. 5, pp. 381-386—English abstract. Relevance can be found in the Japanese Office Action listed below.
Office Action issued in counterpart Japanese Patent Application No. 2019-525489, dated Jul. 26, 2022, 13 pages w/translation.

\* cited by examiner

TOOL FOR MOLDING DYSPHONIA TREATMENT TOOL, AND METHOD FOR BENDING FRONT PIECE OF DYSPHONIA TREATMENT TOOL

TECHNICAL FIELD

The present invention relates to a jig for forming a dysphonia treatment tool and a method for bending a front piece of a dysphonia treatment tool.

BACKGROUND ART

To improve spasmodic dysphonia including a state of the vocal cords failed to vibrate due to excessive glottic closure, a dysphonia treatment tool described in, for example, PTL 1 below is proposed. The dysphonia treatment tool disclosed in PTL 1 includes two titanium clamping sections clamping cut ends on both sides of incised thyroid cartilage and a titanium bridging section bridging the two clamping sections to maintain an incision space of the incised thyroid cartilage. Each of the clamping sections includes a front piece disposed on a front surface side of the incised thyroid cartilage and a rear piece disposed on a rear surface side of the thyroid cartilage.

To use this dysphonia treatment tool, the front piece of each clamping section is bent at first. This causes the shape of the front piece of the dysphonia treatment tool to extend along the shape of the area of the thyroid cartilage which the dysphonia treatment tool is placed in. Then, the thyroid cartilage is incised in the midline, the cut ends of the thyroid cartilage are separated by forceps and the like, the clamping sections of the dysphonia treatment tool are fit to the separated cut ends facing each other, and the forceps are removed. Then, the separated cut ends elastically return in a closing direction, and thus the dysphonia treatment tool is securely fixed between the cut ends.

Further, a suture thread is passed through holes formed in the front pieces for the purpose of gripping the dysphonia treatment tool or the like to suture the dysphonia treatment tool to the thyroid cartilage. This allows more reliable prevention of displacement of the placed dysphonia treatment tool at the cut ends. As described above, it is possible to reliably fix the dysphonia treatment tool between the separated thyroid cartilage.

CITATION LIST

Patent Literature

PTL 1: JP 2005-330 A

SUMMARY OF INVENTION

Technical Problem

As just described, prior to placement of the dysphonia treatment tool in the thyroid cartilage of a patient, the front pieces of the clamping sections have to be bent in advance to extend along the front surface of the thyroid cartilage. However, due to the holes formed in the front pieces, manual bending of the front pieces by a doctor or the like using a conventional tool, such as pliers, sometimes causes bending on a line through a hole. In this case, after placing the dysphonia treatment tool in the thyroid cartilage, there is a possibility that the stress of the bending is concentrated on the line through the hole, and as a result, the front piece is broken on the line through the hole.

It is thus an object of the present invention to provide a jig for forming a dysphonia treatment tool, the tool being capable of bending a front piece in a position not through a hole.

Solution to Problem

A jig of the present invention for forming a dysphonia treatment tool by deformation, the dysphonia treatment tool including: a plurality of clamping sections each having a front piece disposed on a front surface of incised thyroid cartilage and a rear piece disposed on a rear surface of the thyroid cartilage, the clamping sections configured to be fit to respective cut ends of the thyroid cartilage facing each other; and a bridging section linking the clamping sections to each other, the front piece having a hole formed therein, the forming jig comprising a clip section including a pair of maintaining sections configured to sandwich the front piece from both surfaces of a front surface and a back surface thereof to cover at least a portion of the hole.

The present invention allows bending of the front piece while the hole in the front piece is covered with the clip section and it is thus possible to prevent bending in a position where the hole in the front piece is formed.

In the forming jig of the present invention, at least one of the pair of maintaining sections may be formed thick and may have an inclined surface with a thickness dimension gradually decreasing towards an end edge.

This configuration facilitates bending of the treatment tool set in the forming jig.

In the forming jig of the present invention, the pair of maintaining sections may include a plurality of maintaining sections to cover the front piece as one of the pair provided with a space at respective ends, facing each other, of the other maintaining section to have the front piece mounted thereon.

This configuration allows bending of the treatment tool using a plurality of such forming jigs.

In the forming jig of the present invention, one of the pair of maintaining sections to have the front piece mounted thereon may have a front surface with a linear groove formed along an end edge of the other maintaining section facing the former maintaining section to cover the front piece.

This configuration allows reduction in friction between the forming jig and the treatment tool set therein to avoid minute flaws and the like in the treatment tool.

In the forming jig of the present invention, the maintaining section to cover the front piece as one of the pair may have an end with a side wall formed intersecting this maintaining section and extending in an L shape, and the side wall and the maintaining section to cover the front piece may have an intersection with an inner wall notched substantially cylindrically.

In the forming jig of the present invention, the maintaining section to cover the front piece as one of the pair may have a longitudinal direction defined as a direction orthogonal to a direction of disposing the front piece and may have a width dimension varying in the longitudinal direction to allow selection of a dimension to cover the front piece.

This configuration allows application to multiple types of treatment tool differing in position and size of the hole in the front piece.

In the forming jig of the present invention, the width dimension of the maintaining section to cover the front piece as one of the pair may vary at a corner notched substantially cylindrically.

In the forming jig of the present invention, the pair of maintaining sections may have maintaining surfaces facing each other, either one of the maintaining surfaces having a protrusion formed to be inserted into the hole.

This configuration facilitates positioning of the forming jig to the front piece.

In the forming jig of the present invention, the clip section may include a storage section capable of disposing the bridging section.

This configuration increases the degrees of freedom in the direction of disposing the front piece relative to the clip section.

In the forming jig of the present invention, the clip section includes a pressing member to press and bend the front piece sandwiched by the clip section.

This configuration allows completion of bending by one forming jig.

In the forming jig of the present invention, the pair of maintaining sections may have maintaining surfaces facing each other with a recess formed to allow fitting of a portion of the front piece.

This configuration facilitates placement of the front piece on the forming jig.

The forming jig of the present invention may further include a locking section to fix the pair of maintaining sections to each other.

This configuration allows reliable fixation of the clip section.

The forming jig of the present invention may further include an operating section to operate the clip section.

This configuration facilitates operation of the clip section.

In the forming jig of the present invention, the operating section may be a lever cooperating with the pair of maintaining sections openably formed via a pivot to open and close the pair of maintaining sections.

This configuration facilitates operation of the maintaining sections.

A method for bending a front piece of a dysphonia treatment tool of the present invention, the dysphonia treatment tool including a plurality of clamping sections each having a flat-plate front piece disposed on a front surface of incised thyroid cartilage and a rear piece disposed on a rear surface of the thyroid cartilage, the clamping sections configured to be fit to respective cut ends of the thyroid cartilage facing each other, and including a bridging section linking the clamping sections to each other, the front piece having a hole formed therein, the method includes: temporarily setting a linear bending line in a position without overlapping the hole in the front piece; sandwiching a portion of the front piece by a clip section including a pair of maintaining sections configured to sandwich the front piece by partially covering front and back surfaces of the front piece to cause a remaining portion of the front piece to project; causing one of side edges of the maintaining sections to extend along the bending line; and holding the remaining portion of the front piece to bend the front piece about the side edge.

The present invention allows bending of the front piece while the hole in the front piece is covered with the clip section and it is thus possible to prevent bending in a position where the hole in the front piece is formed.

Advantageous Effects of Invention

The forming jig and the method for bending a front piece of a dysphonia treatment tool of the present invention allow bending of the front piece of the dysphonia treatment tool in a position not through the hole and thus exhibit the effect of reducing the possibility of breakage due to metal fatigue during bending of the front piece or after fixation to the thyroid cartilage by suture. They further exhibit the effect of facilitating control of force during bending.

DESCRIPTION OF EMBODIMENTS

Embodiments of a jig for forming a dysphonia treatment tool of the present invention are described with reference to the drawings.

Figure 1:
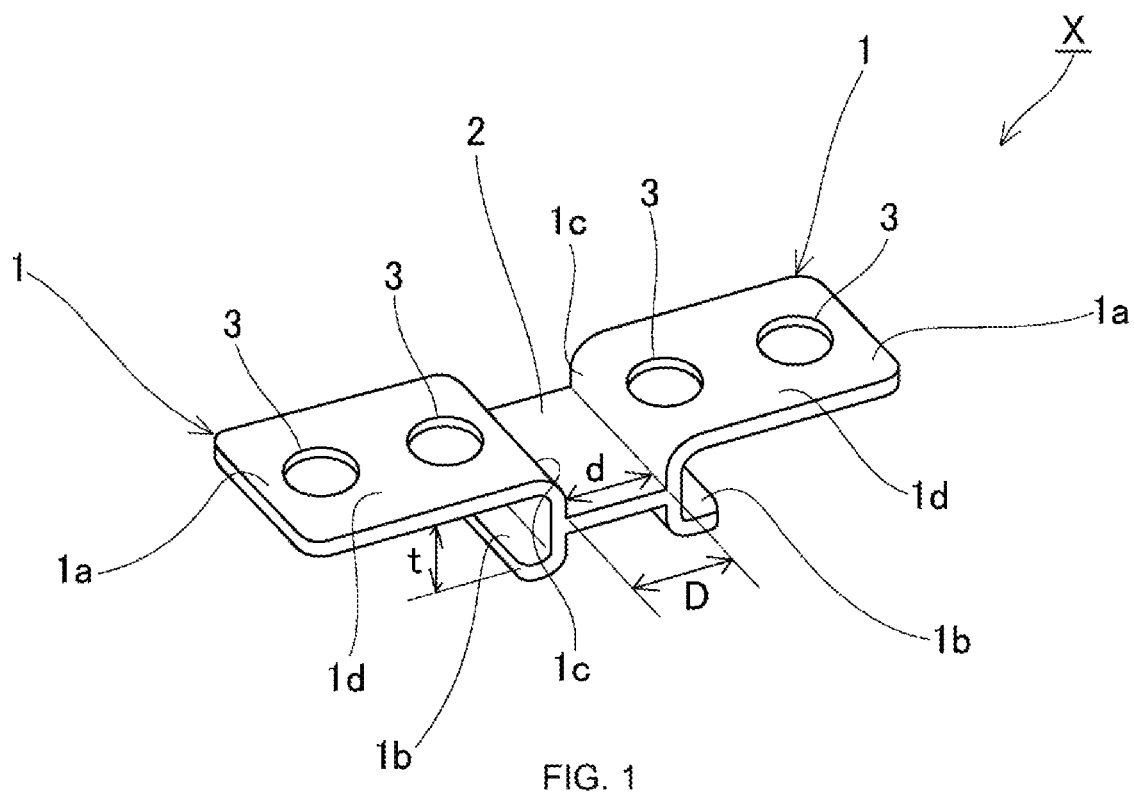
FIG. 1 is a perspective view illustrating a dysphonia treatment tool to be an object used by a forming jig of the present invention.
Figure 2:
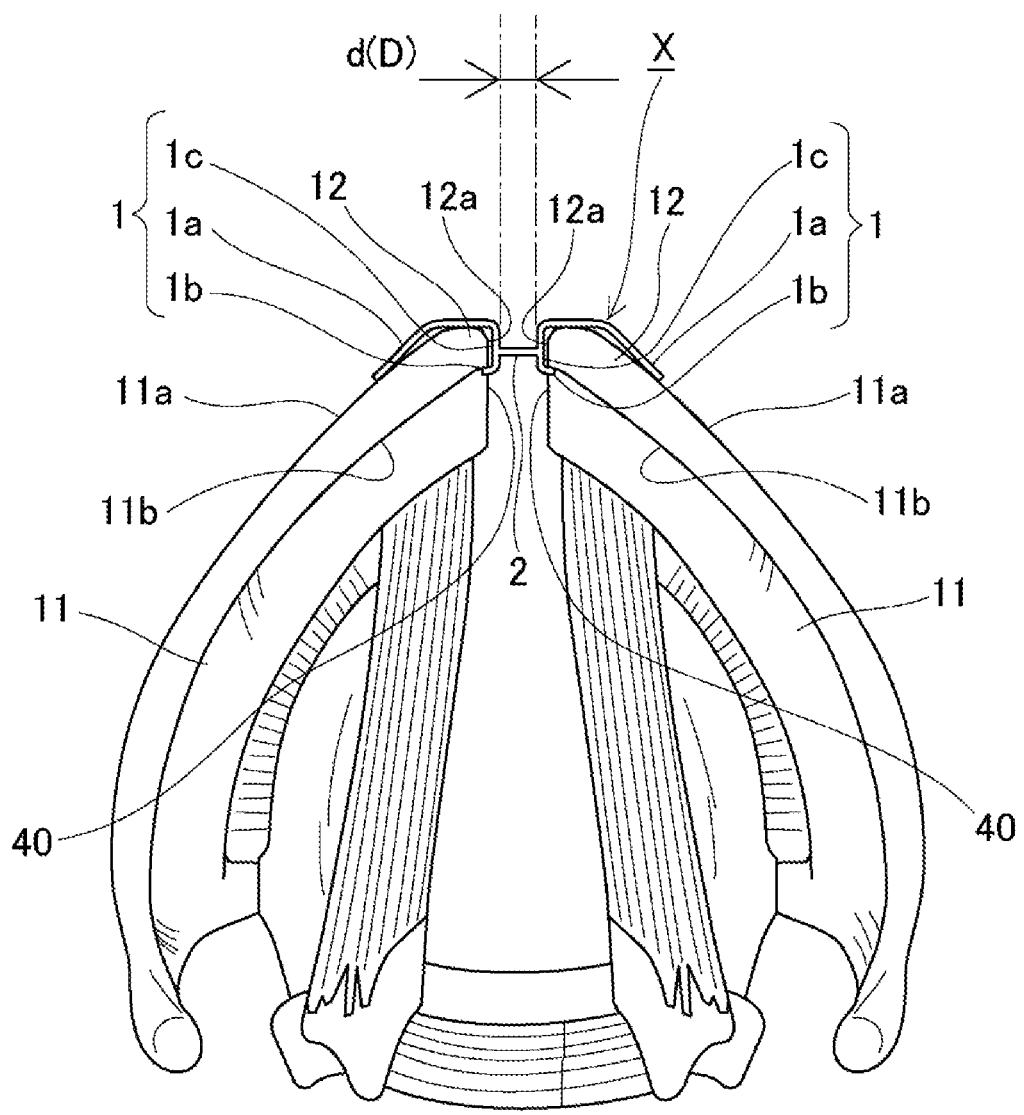
FIG. 2 is a bottom view illustrating a state of the dysphonia treatment tool to be an object used by the forming jig of the present invention placed in the thyroid cartilage.

A jig for forming a dysphonia treatment tool (hereinafter, referred to as a "treatment tool") in the first embodiment of the present invention bends a front piece 1a of a treatment tool X illustrated in FIG. 1 at a predetermined angle, for example, as illustrated in FIG. 2.

The treatment tool X is first described to be an object formed by the forming jig of the present invention.

As illustrated in FIG. 1, the treatment tool X includes: a plurality (in the present embodiment, one pair) of clamping sections 1, 1 each having the front piece 1a and a rear piece 1b and being configured to be fit to respective cut ends 12, 12, facing each other, of the incised thyroid cartilage 11 illustrated in FIG. 2; and a bridging section 2 linking the clamping sections 1, 1.

The front piece 1a is formed in a substantially strip-like plate shape in a plan view and includes an end surface portion 1c and a front surface contacting portion 1d. The end surface portion 1c is on a base end side of the front piece 1a in a longitudinal direction and is configured to be bent to face a cut end surface 12a of the thyroid cartilage 11 illustrated in FIG. 2. The front surface contacting portion 1d is on a distal end side relative to the end surface portion 1c of the front piece 1a and is configured to be disposed on a front surface 11a of the thyroid cartilage 11.

In the front piece 1a, a plurality (in the present embodiment, two) of holes 3 are formed at an interval in the longitudinal direction. The holes 3, 3 allow insertion of a suture thread (not shown, hereinafter the same) therein and are formed in the size from 1.0 mm to 2.0 mm to allow insertion of a suture needle therein.

As illustrated in FIG. 1 and FIG. 2, the rear piece 1b is bent from the end surface portion 1c of the front piece 1a towards a rear surface 11b side of the thyroid cartilage 11 illustrated in FIG. 2.

The front piece 1a and the rear piece 1b are integrally formed to constitute the clamping section 1, and the entire clamping section 1 is formed in a substantially J shape (inverted J shape).

In the clamping sections 1, 1, the front piece 1a may have a length that is necessary and sufficient for clamping the thyroid cartilage 11 and can extend along the form of the thyroid cartilage 11. Specifically, the length is preferably set approximately from 8 mm to 12 mm. The rear piece 1b preferably has a length to allow contact from an end edge of the cut end 12 of the thyroid cartilage 11 to an end edge of a soft tissue 40 under the thyroid cartilage 11. Specifically, the rear piece 1b preferably has a length approximately from 1.5 mm to 3.5 mm.

As illustrated in FIG. 2, the pair of clamping sections 1 is provided in bilateral symmetry each having the front piece 1a disposed on the front surface 11a side of the thyroid cartilage 11 and the cut end surface 12a and the rear piece 1b disposed on the rear surface 11b side of the thyroid cartilage 11 to allow fitting to the respective cut ends 12, 12 of the thyroid cartilage 11 facing each other. The pair of clamping sections 1, 1 are linked by the bridging section 2.

As illustrated in FIG. 1, the bridging section 2 is a section linking the clamping sections 1 and links the clamping sections 1 in an intermediate section in an extending direction of the end surface portion 1c. The bridging section 2 has a length (d), that is, a space D between both clamping sections 1, 1 equivalent to a distance between the cut ends 12, 12 of the separated thyroid cartilage 11 illustrated in FIG. 2 and, while the length (d) differs depending on symptoms, body types, and vocal states of patients with dysphonia, the length (d) is generally set in the range from 2 to 6 mm.

The clamping sections 1 and the bridging section 2 are both composed of titanium.

A titanium metal used for the treatment tool X to be an object used by a forming jig 20A is not limited to titanium as a pure metal and includes titanium alloys used for artificial bones, artificial joints, and dental implants as biocompatible metal materials. Specifically, it is possible to use Ti-6A1-4V or the like that does not contain Ni, which is indicated as a cause of cancer and allergies, and is known as a titanium alloy excellent in biocompatibility. To prevent wear and elution, the titanium or the titanium alloy may be surface modified by ion implantation of N or C.

The front surface contacting portion 1d and the rear piece 1b preferably have a space (width dimension of the end surface portion 1c) t between them slightly greater than a thickness dimension of the thyroid cartilage 11 illustrated in FIG. 2, and specifically the space t is preferably from 2 to 4 m approximately. If the space t is less than the thickness dimension of the thyroid cartilage 11 illustrated in FIG. 2, the thyroid cartilage 11 is squeezed and the clamping sections 1 continually presses the thyroid cartilage 11 for a long period of time, causing a possibility of wear and damage to the thyroid cartilage 11. In contrast, if the space t between the front surface contacting portion 1d and the rear piece 1b is excessively large in comparison with the thickness dimension of the thyroid cartilage 11, the thyroid cartilage 11 is substantially difficult to clamp and the clamping sections 1 are relatively liable to position shifting (sliding) with respect to the thyroid cartilage 11.

The configuration of the forming jig 20A is then described.

Figure 3:
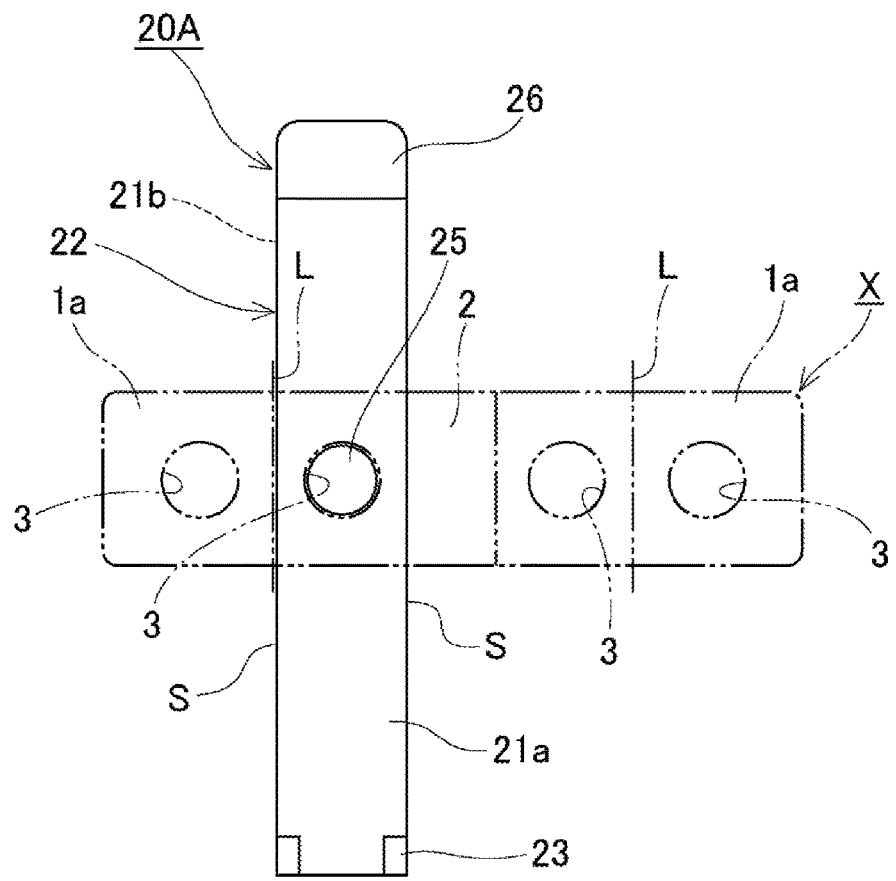
FIG. 3 is a plan view illustrating a state of folding a forming jig given as a first embodiment of the present invention.
Figure 4:
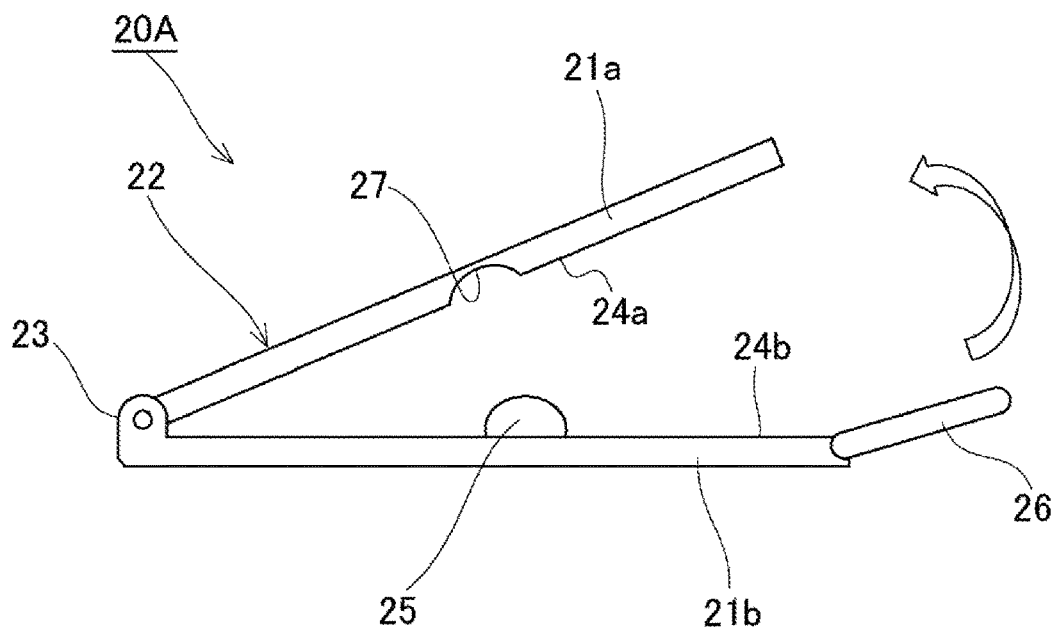
FIG. 4 is a side view illustrating a state of unfolding the forming jig given as the first embodiment of the present invention.

As illustrated in FIG. 3 and FIG. 4, the forming jig 20A includes a pair of maintaining sections 21a, 21b configured to sandwich the front piece 1a to cover the hole 3 on a base end side of the front piece 1a and both peripheral surfaces of the front surface and the back surface. The pair of maintaining sections 21a, 21b facing each other constitutes a clip section 22.

Figure 5:
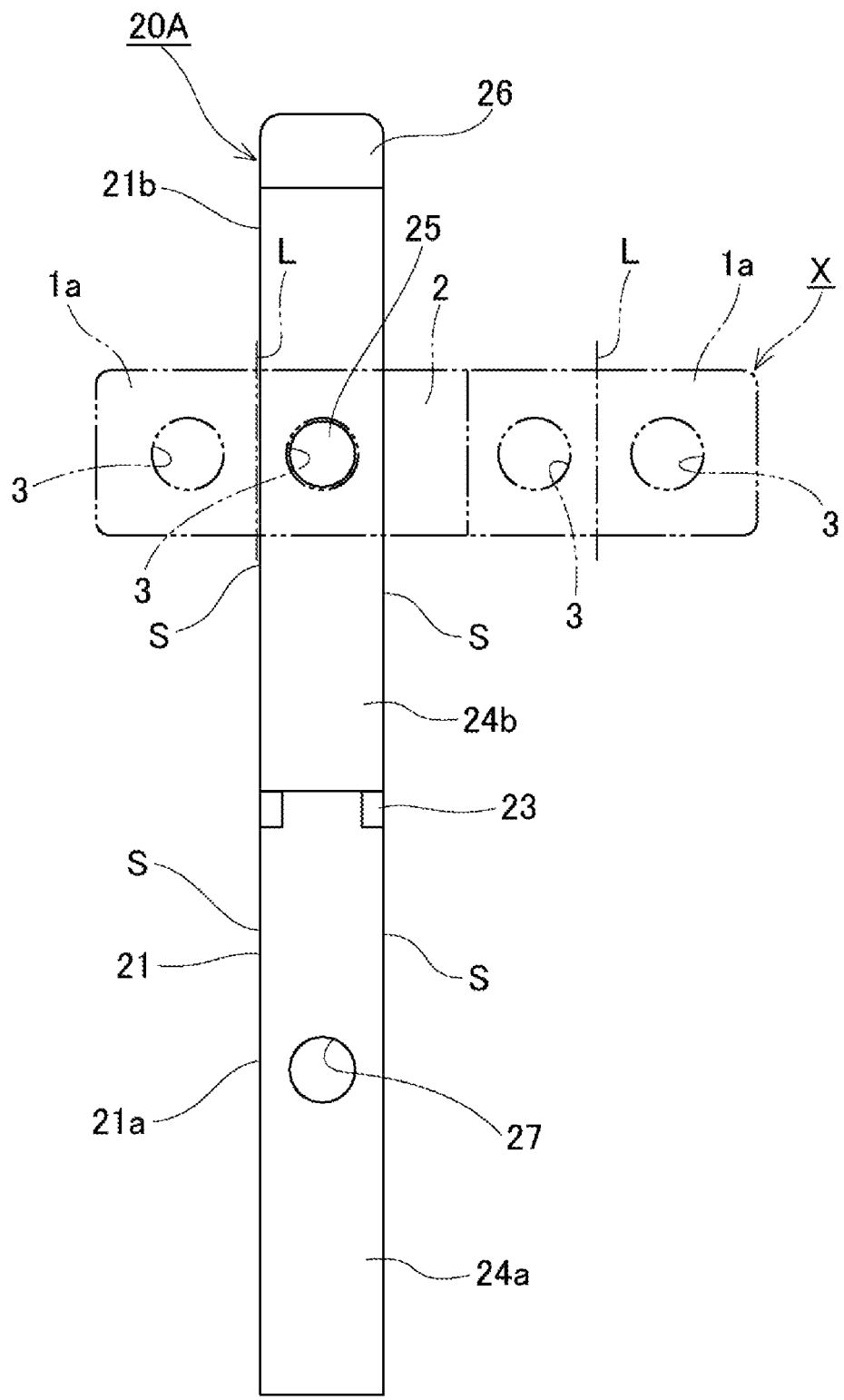
FIG. 5 is a plan view illustrating a state of unfolding the forming jig given as the first embodiment of the present invention.

As illustrated in FIG. 4, the maintaining sections 21a, 21b are both formed in a rectangular plate shape with a material, such as metal and a highly rigid synthetic resin. As illustrated in FIG. 5, each maintaining section 21 has side edges S formed in an approximately linear shape. The maintaining sections 21a, 21b are linked via a hinge 23 at one end in the longitudinal direction. The maintaining section 21a is a movable side maintaining section 21a to rotate via the hinge 23, and the maintaining section 21b is a fixed side maintaining section 21b.

The fixed side maintaining section 21b and the movable side maintaining section 21a are formed to overlap each other provided with a space (allowance) that allows the front piece 1a of the treatment tool X to be sandwiched in the thickness direction and reliably maintained.

As illustrated in FIG. 4 and FIG. 5, the fixed side maintaining section 21b in contact with the front piece 1a has a maintaining surface 24b with a protrusion 25 formed to allow insertion into the holes 3 in the front piece 1a illustrated in FIG. 1. The protrusion 25 is formed in accordance with the shape and size of the holes 3 and provided less likely to oscillate in a horizontal direction while the protrusion 25 is inserted into any of the hole 3. The fixed side maintaining section 21b has a distal end provided with a locking section 26 to maintain the state of being overlapped by the movable side maintaining section 21a. The locking section 26 is a fastener to be fastened at the distal end of the movable side maintaining section 21a overlapping the fixed side maintaining section 21b by rotation not to unintentionally rotate. It should be noted that the locking section 26 is not essential.

The movable side maintaining section 21a in contact with the front piece 1a has a maintaining surface 24a with a depression 27 formed to be fit to the protrusion 25 in a position corresponding to the protrusion 25. When the protrusion 25 has a projected height equal to the thickness of the front piece 1a or less, the depression 27 may be omitted.

The movable side maintaining section 21a and the fixed side maintaining section 21b have a width dimension not particularly limited as long as the side edges S can be positioned between the holes 3, 3 while covering the hole 3 on the base end side of the front piece 1*a* and the periphery. For example, the dimensions are preferably 5 mm or more and 60 mm or less in the longitudinal direction and 2.5 mm or more and 5 mm or less in the transverse direction. The space (allowance to insert the front piece 1*a*) between the movable side maintaining section 21*a* and the fixed side maintaining section 21*b* is preferably set at 0.1 mm or more and 0.4 mm or less.

A method of use, the action, the functions, and the effects of the forming jig 20A are then described.

To use the forming jig 20A, as illustrated in FIG. 4 and FIG. 5, the movable side maintaining section 21*a* is rotated to be opened and the front piece 1*a* is disposed on the fixed side maintaining section 21*b* by fitting the hole 3 on the base end side of the front piece 1*a* to the protrusion 25 of the fixed side maintaining section 21*b* in such a manner that the longitudinal direction of the front piece 1*a* is substantially orthogonal to the longitudinal direction of the fixed side maintaining section 21*b*.

While being then rotated as illustrated in FIG. 3 and sandwiching the front piece 1*a*, the movable side maintaining section 21*a* overlaps the fixed side maintaining section 21*b* and the locking section 26 fixes the movable side maintaining section 21*a* to the fixed side maintaining section 21*b*.

In this manner, the hole 3 on the base end side of the front piece 1*a* of the treatment tool X maintained by the forming jig 20A is covered with the forming jig 20A, and the distal end of the front piece 1*a* sticks out of the side edge S of the maintaining section 21.

When the distal end of the front piece 1*a* projecting from the forming jig 20A is maintained in this state and bent, the front piece 1*a* is bent in the position along the side edge S of the clip section 22 without being bent around the hole 3 covered with the clip section 22 due to the clip section 22 formed with the highly rigid material.

Accordingly, an effect is exhibited that allows prevention of breakage of the front piece 1*a* in an area where the rigidity is reduced due to bending of the front piece 1*a* on a line through the hole 3.

In addition, although the present embodiment describes the case as an example where, as illustrated in FIG. 2, the side edges S of the maintaining sections 21 are set between the holes 3, 3 in the front piece 1*a* and an area between the holes 3,3 is bent, the front piece 1*a* is preferably bent in two areas of an area between the bridging section 2 and the hole 3 closest to the bridging section 2, that is, the base end of the front surface contacting portion 1*d* of the front piece 1*a* and an area between the holes 3. When the front piece 1*a* is thus bent in the two areas of the base end of the front surface contacting portion 1*d* and the approximate center of the front surface contacting portion 1*d* between the holes 3, 3, it is possible to facilitate fitting of the front piece 1*a* to the front surface 11*a* of the thyroid cartilage 11 and to bend the front piece 1*a* more gently.

While the front piece 1*a* is bent, the distal end side of the front piece 1*a* projecting from the forming jig 20A may be sandwiched by another forming jig 20A to bend an area between the holes 3, 3 by gripping the forming jigs 20A, 20A.

Figure 6:
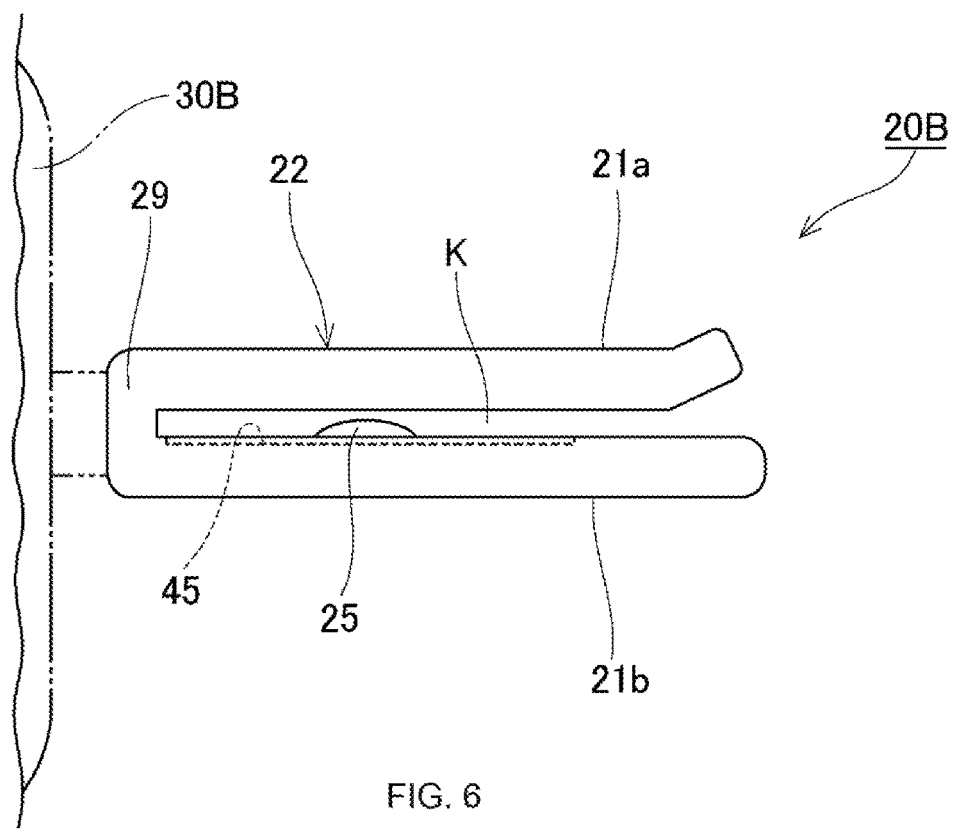
FIG. 6 is a side view of a forming jig given as a second embodiment of the present invention.
Figure 7:
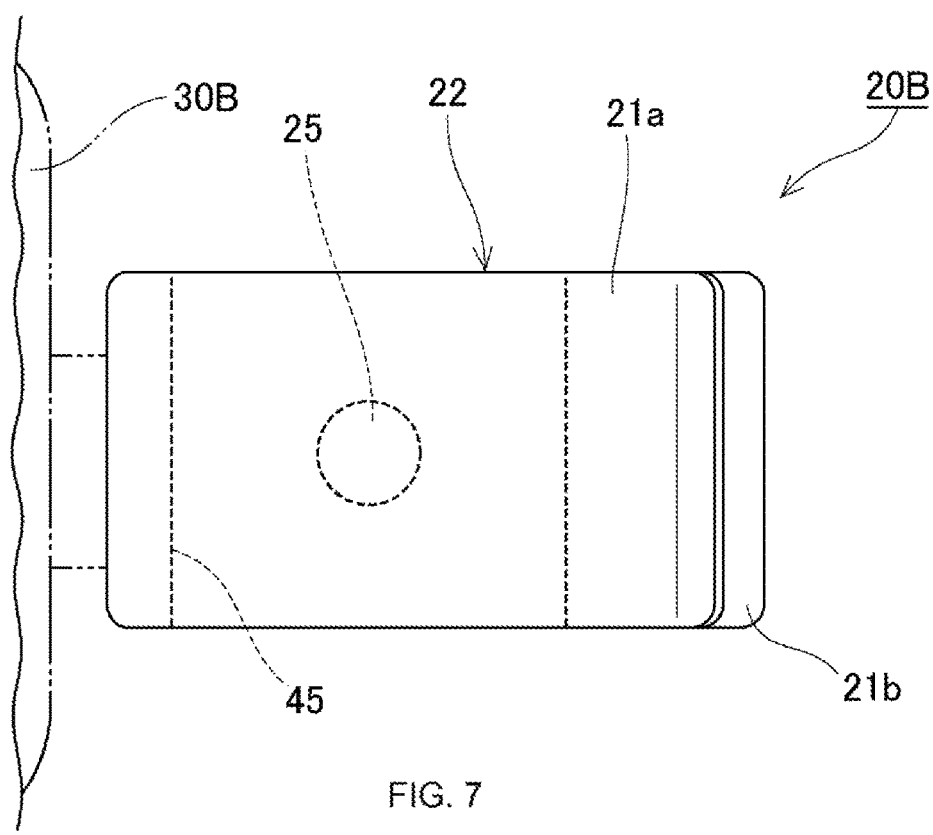
FIG. 7 is a plan view of the forming jig given as the second embodiment of the present invention.

With reference to FIG. 6 and FIG. 7, a forming jig 20B in the second embodiment of the present invention is then described.

In the present embodiment, the description in common with the forming jig 20A in the first embodiment is omitted to mainly describe differences.

As illustrated in FIG. 6, the forming jig 20B in the present embodiment differs from the forming jig 20A in the first embodiment in the configuration where the space between the maintaining section 21*a* and the maintaining section 21*b* facing each other is fixed and both maintaining sections 21*a*, 21*b* do not rotate about a base end 29.

The maintaining sections 21*a*, 21*b* are formed in a shape of one long rectangular plate bent to provide an internal space K equivalent to or slightly smaller than a thickness dimension of the front piece 1*a* of the treatment tool X.

The maintaining section 21*a* not provided with the protrusion 25 has a distal end bent to facilitate insertion of the front piece 1*a*.

The maintaining section 21*a* and the maintaining section 21*b* are formed in a manner integrated in the base end 29 in a fixed shape and each can be internally biased.

The maintaining section 21*b* has a recess 45 allowing the front piece 1*a* to be fit.

This configuration causes the maintaining sections 21*a*, 21*b*, when the front piece 1*a* of the treatment tool X is inserted between the maintaining sections 21*a*, 21*b*, to bias both the front surface and the back surface of the front piece 1*a* without being press separated by the thickness of the front piece 1*a* and, while the front piece 1*a* comes close to and passes over the protrusion 25, to bias even more strongly. Due to the biasing force, the maintaining sections 21*a*, 21*b* then fit the protrusion 25 to the hole 3 when the hole 3 in the front piece 1*a* comes close to the protrusion 25 and again bias the front surface and the back surface of the front piece 1*a* to maintain the front piece 1*a*.

Accordingly, the forming jig 20B not only exhibits the action, the functions, and the effects same as the forming jig 20A in bending of the front piece 1*a* but also exhibits the effect of securely maintaining the front piece 1*a* without using the locking section 26 to fix the distal ends of the maintaining sections 21 to each other.

In addition, the forming jig 20B exhibits the effect of readily allowing the front piece 1*a* to be maintained only by inserting the front piece 1*a* between the maintaining sections 21*a*, 21*b* while omitting the operation of rotating the maintaining section 21*a*.

Still in addition, the configuration of engaging the protrusion 25 of the maintaining section 21*b* with the hole 3 in the front piece 1*a* causes reliable positioning of the maintaining sections 21*a*, 21*b* relative to the front piece 1*a* and thus exhibits the effect of allowing reliably bending of the front piece 1*a* in an area between the holes 3, 3 even when one of the holes 3 is covered with the maintaining section 21*a* and is not visible.

Both in the forming jigs 20A in the first embodiment and 20B in the second embodiment, the clip section 22 may have an operating section 30B mounted to the base end 29 of the clip section 22 to facilitate manual gripping. The operating section 30B may be in any shape as long as the shape facilitates operation of the clip section 22 and may be formed in, for example, a rod shape to facilitate gripping with the entire palm or the palm and fingertips by a person handling the forming jig 20A or 20B.

Figure 8:
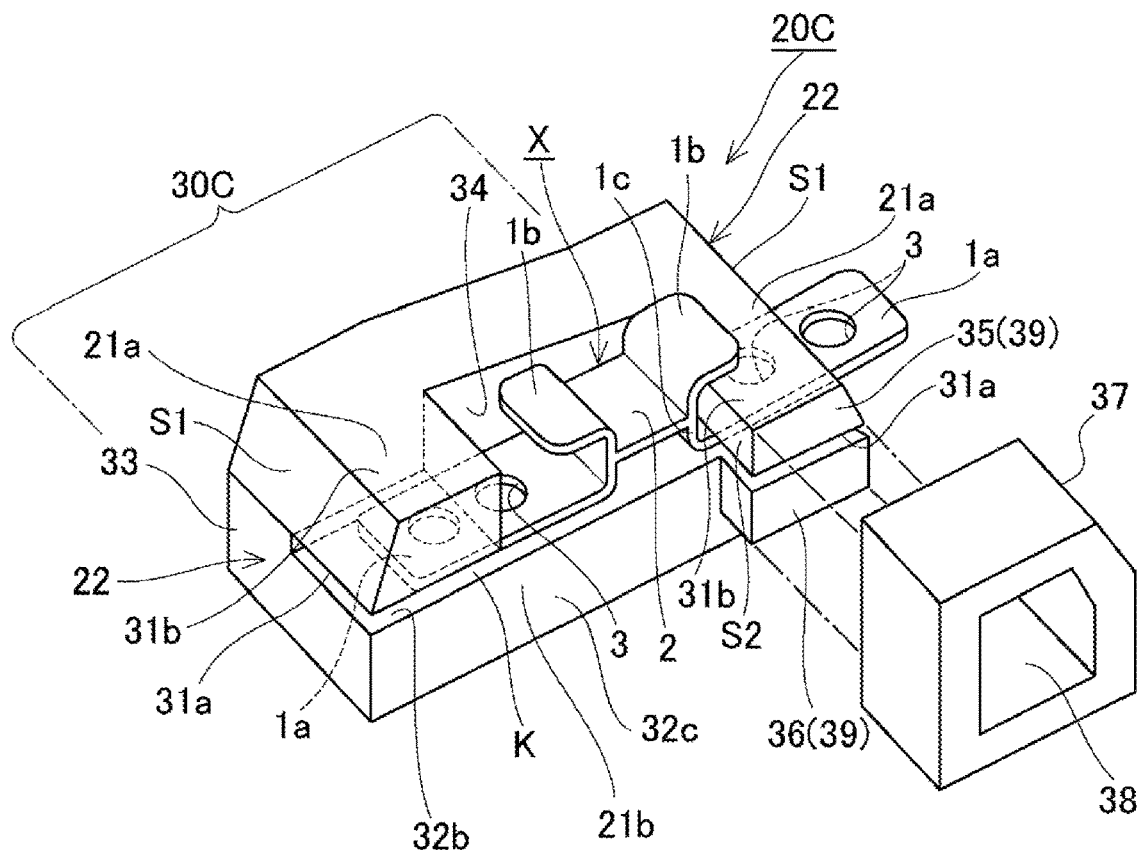
FIG. 8 is a perspective view of a forming jig given as a third embodiment of the present invention.
Figure 9:
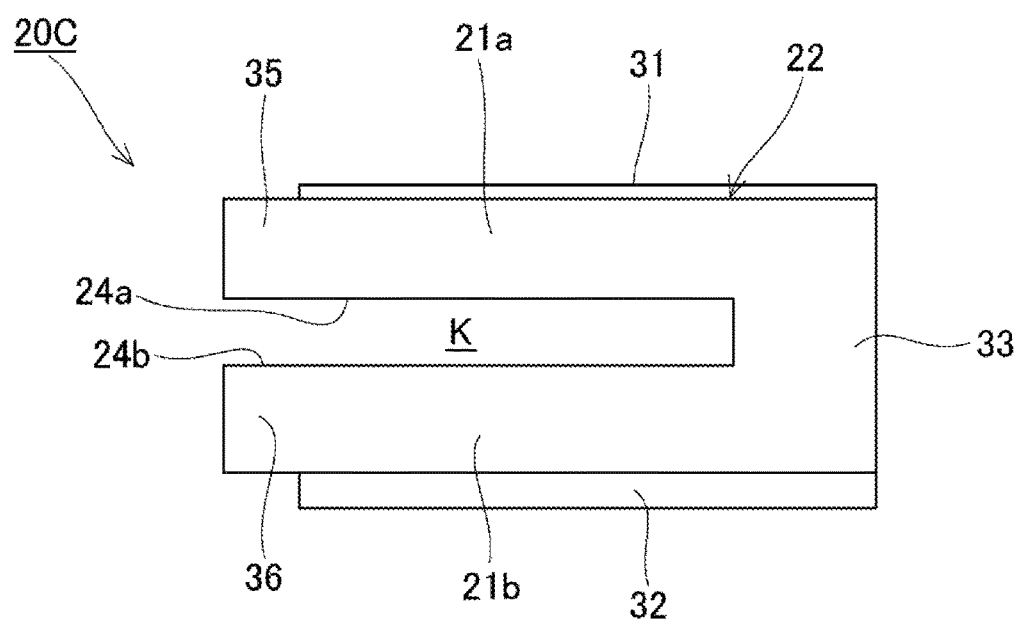
FIG. 9 is a side view of the forming jig given as the third embodiment of the present invention.
Figure 10:
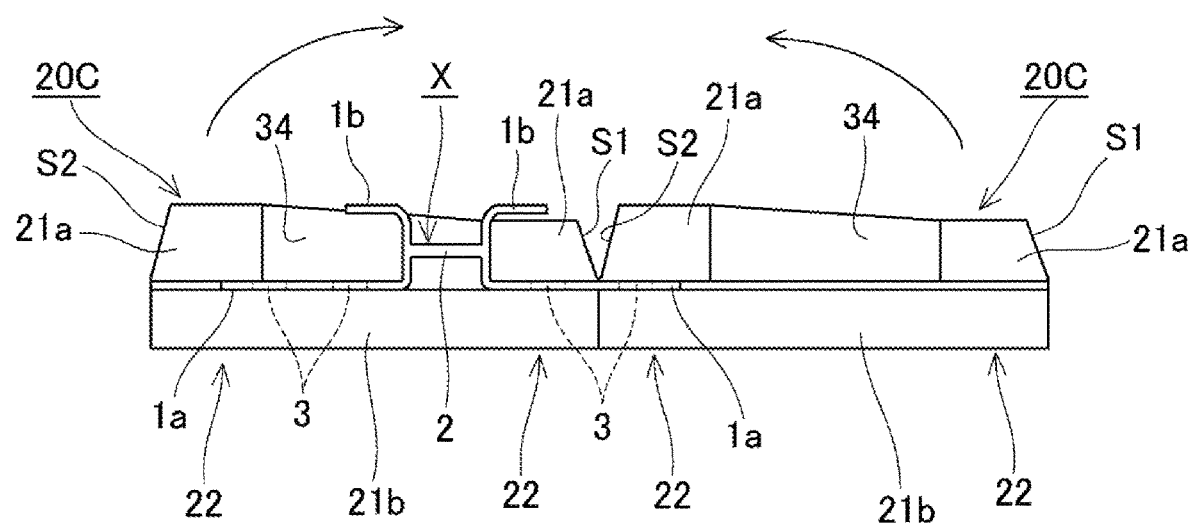
FIG. 10 is a diagram illustrating a method for using the forming jig given as the third embodiment of the present invention.

With reference to FIGS. 8-10, a forming jig 20C in the third embodiment of the present invention is then described.

The forming jig 20C in the present embodiment is an application example of the forming jig 20B in the second embodiment, and the description in common with the second embodiment is omitted to mainly describe differences.

As illustrated in FIG. 8 and FIG. 9, the forming jig 20C is common with the forming jig 20B in the second embodiment in that the maintaining section 21a and the maintaining section 21b of the clip section 22 are integrally formed and the area between the maintaining section 21a and the maintaining section 21b is fixed. The forming jig 20C, however, mainly differs from the forming jig 20B in the following points.

That is, the forming jig 20C has the maintaining section 21b (hereinafter, referred to as a "lower maintaining section 21b") to receive the front surface side of the front piece 1a provided with maintaining sections 21a (hereinafter, referred to as "upper maintaining sections 21a") at both ends of one end and another end opposite to the former end of the lower maintaining section 21b. The lower maintaining section 21b is formed in a substantially flat plate shape in a size to allow reception of at least a portion of both front pieces 1a, 1a. The portions other than the upper maintaining sections 21a and the lower maintaining section 21b used for bending of the front piece 1a provide an operating section 30C for gripping and operation of the forming jig 20C.

The differences of the forming jig 20C from the forming jig 20B are specifically described below.

As illustrated in FIG. 8, the forming jig 20C includes the lower maintaining section 21b in a substantially rectangular shape in a plan view, a linking section 33 rising from an end along one side of the lower maintaining section 21b, and the upper maintaining sections 21a, 21a extending from an upper end of the linking section 33 in a direction facing the lower maintaining section 21b.

The lower maintaining section 21b is formed in a substantially rectangular flat plate shape in a size to allow placement of at least a portion of the respective front pieces 1a, 1a. Specifically, the lower maintaining section 21b is formed in a size, when the pair of front pieces 1a, 1a are mounted to cause the distal end of the front piece 1a to project from a portion intended to be bent, to locate at least a portion of the other front piece 1a on the lower maintaining section 21b. In this situation, the whole of the other front piece 1a may be disposed on the lower maintaining section 21b or the distal end of the other front piece 1a may project from the lower maintaining section 21b.

The linking section 33 rises from an end along one side of the lower maintaining section 21b at a substantially right angle to form a side wall and forms a certain gap between the lower maintaining section 21b and the upper maintaining sections 21a. The linking section 33 has a side wall 34a facing a direction of the distal ends of the upper maintaining sections 21a rising vertically and the side wall 34a forms a portion of a storage section 34 described later and catches an end of the treatment tool X when the treatment tool X is inserted.

The upper maintaining sections 21a, 21a project in a plate shape from upper ends at both ends in a direction along one side of the linking section 33 (i.e., direction to dispose the front pieces 1a, 1a) so as to face the lower maintaining section 21b. That is, the upper maintaining sections 21a, 21a are provided with a space between them. The upper maintaining sections 21a, 21a and the linking section 33 are formed in a substantially U shape in a plan view. The storage section 34 has a notch-like shape formed by the upper maintaining sections 21a, 21a and the linking section 33 and is capable of disposing the bridging section 2.

The upper maintaining sections 21a, 21a have maintaining surfaces (i.e., surfaces facing the lower maintaining section 21b) 31a, 31a formed flush with each other and forming a groove K penetrating between the lower maintaining section 21b and the maintaining surfaces 31a, 31a in one direction. The groove K allows insertion of the treatment tool X.

Each upper maintaining section 21a has a side end surface S1 on the side to cause the front piece 1a to project and the side end surface S1 forms an inclined surface where the width dimension of the upper maintaining section 21a gradually decreases from the maintaining surface 31a towards an upper surface 31b.

The distance between the upper maintaining sections 21a, 21a is formed, when the front pieces 1a are inserted into the groove K to dispose the bridging section 2 in the storage section 34 and cause the distal end of one of the front piece 1a to project from one of the upper maintaining sections 21a, to cover a portion of the other front piece 1a with the other upper maintaining section 21a. The present embodiment is configured to, while the front piece 1a is in the above state, cause the other front piece 1a to be entirely disposed on the lower maintaining section 21b and to have the distal end covered with the upper maintaining section 21a.

One of the upper maintaining sections 21a is formed thicker than the other upper maintaining section 21a. In other words, since one of the upper maintaining sections 21a has the maintaining surface 31a formed flush with that of the other upper maintaining section 21a, the former one of the upper maintaining sections 21a has a height higher than the height of the other upper maintaining section 21a. The linking section 33 accordingly becomes gradually thicker from one of the upper maintaining sections 21a towards the other upper maintaining section 21a.

The upper maintaining section 21a formed thinner has a protrusion 35 formed at the distal end in the extending direction, and the lower maintaining section 21b has a protrusion 36 formed to face the protrusion 35. The protrusions 35, 36 project from a position equivalent to an end surface 32c of the lower maintaining section 21b.

The protrusions 35, 36 constitute a locking section 39 to be fit into a ring-shaped locking member 37. The protrusions 35, 36 and the locking member 37 provide a mechanism to prevent elastic deformation of the upper maintaining section 21a in the opening direction during bending of the front piece 1a.

The locking member 37 has an opening 38 formed to allow insertion of the protrusions 35, 36 for a tight fit. The locking member 37 does not have to be in a ring shape as long as it is possible to prevent enlargement of the space between the upper maintaining section 21a and the lower maintaining section 21b. The locking member 37 may be formed in a U shape capable of sandwiching the protrusions 35, 36.

The upper maintaining sections 21a, 21a may be respectively formed with a thickness of 1.9 mm or more, and they are more preferably formed in accordance with the dimension between the front piece 1a and the rear piece 1b of the treatment tool X to be placed.

The linking section 33 may be formed with a thickness of 3.0 mm or more and preferably formed with a thickness of 3.4 mm or more and 16 mm or less.

The groove K may have a groove width set equivalent to or more than the thickness of the front piece 1a of the treatment tool X and not more than the thickness of the front piece 1a+1 mm.

The lower maintaining section 21b is formed with a thickness slightly, specifically ranging from 1 m or more to 2 mm or less, greater than that of the upper maintaining section 21a.

The forming jig 20C may be formed from any material including synthetic resins and metals, such as stainless steel, as long as being formed from a rigid material.

In the forming jig 20C, the upper maintaining sections 21a, 21a formed as described above are formed to provide a space between themselves at both ends of the lower maintaining section 21b and the portions other than the upper maintaining section 21a side to be used constitute the operating section 30C to facilitate gripping and operation of the forming jig 20C.

A method of use and the action of the forming jig 20C are then described.

To use the forming jig 20C, as illustrated in FIG. 8, the treatment tool X is disposed in the groove K to place the front piece 1a of the treatment tool X on the lower maintaining section 21b side and to put the bridging section 2 in the storage section 34.

When an area between the holes 3, 3 in the front piece 1a is intended to be bent, the end surface portion 1c of the treatment tool X is brought closer to a side end surface S2 of the upper maintaining section 21a to cause the front piece 1a to project from the clip section 22 in such a manner that one of the holes 3 appears from the side end surface S1 side. The width dimension of the upper maintaining section 21a is set to allow positioning of a lower end of the side end surface S1 of the upper maintaining section 21a between the holes 3, 3 in the front piece 1a. Accordingly, while the hole 3 on the base end side of the front piece 1a is covered with the upper maintaining section 21a, the distal end from the area between the holes 3, 3 projects from the side end surface S1 of the upper maintaining section 21a. In this state, the protrusion 35 of the upper maintaining section 21a and the protrusion 36 of the lower maintaining section 21b are fit to the locking member 37 to fix the treatment tool X to the forming jig 20C.

Then, the portions other than the upper maintaining section 21a to cause the front piece 1a to project, that is, the operating section 30C is gripped by the hand and the projected distal end of the front piece 1a is held by pliers or the like to bend the front piece 1a at a desired angle along a lower end edge of the side end surface S1 of the clip section 22.

For bending, as illustrated in FIG. 10, substantially the entire projected area of the front piece 1a may be further sandwiched by a clip section 22 of another forming jig 20C to bend the front piece 1a between the forming jigs 20C, 20C.

Bending of the front piece 1a in such a manner allows bending of the front piece 1a in accordance with the shape of the thyroid cartilage in an area between the holes 3, 3 having a sufficient width dimension in the front piece 1a without bending around the hole 3 on the base end side of the front piece 1a. In particular, when the front piece 1a is bent using the two forming jigs 20C as illustrated in FIG. 10, it is possible to cover the holes 3, 3 in the front piece 1a with the respective two forming jigs 20C for bending and thus to bend the area between the holes 3, 3 more readily.

Accordingly, such bending exhibits the effect of allowing avoidance of breakage of the front piece 1a due to bending of the front piece 1a on a line through the hole 3 in the area having a smaller width dimension of the front piece 1a.

When the front piece 1a is intended to be bent on the base end side with respect to the hole 3 on the base end side of the front piece 1a, the front piece 1a is inserted into the groove K from the side end surface S1 side to cause the bridging section 2 and the other front piece 1a to project from the side end surface S1. An area near the bridging section 2 is then gripped to bend the base end of the front piece 1a.

Use of the forming jig 20C in such a manner allows bending of the front piece 1a in the area closest to the base end of the front piece 1a and avoiding the holes 3.

The forming jig 20C is also configured to allow holding of the operating section 30C containing approximately the entire treatment tool X and to cause only the distal end of the front piece 1a intended to be bent to project. Accordingly, the forming jig 20C exhibits the effect of allowing facilitation and stabilization of bending of the front piece 1a.

The forming jig 20C is also capable of fixing the protrusions 35, 36 by the locking member 37 and thus exhibits the effect of allowing prevention of deformation of the upper maintaining sections 21a and the lower maintaining section 21b during bending.

The locking member 37 described in the present embodiment is not essential when the fixation is reliable by sandwiching the clip section 22 or the clip section 22 has the rigidity less likely to be deformed.

Figure 11:
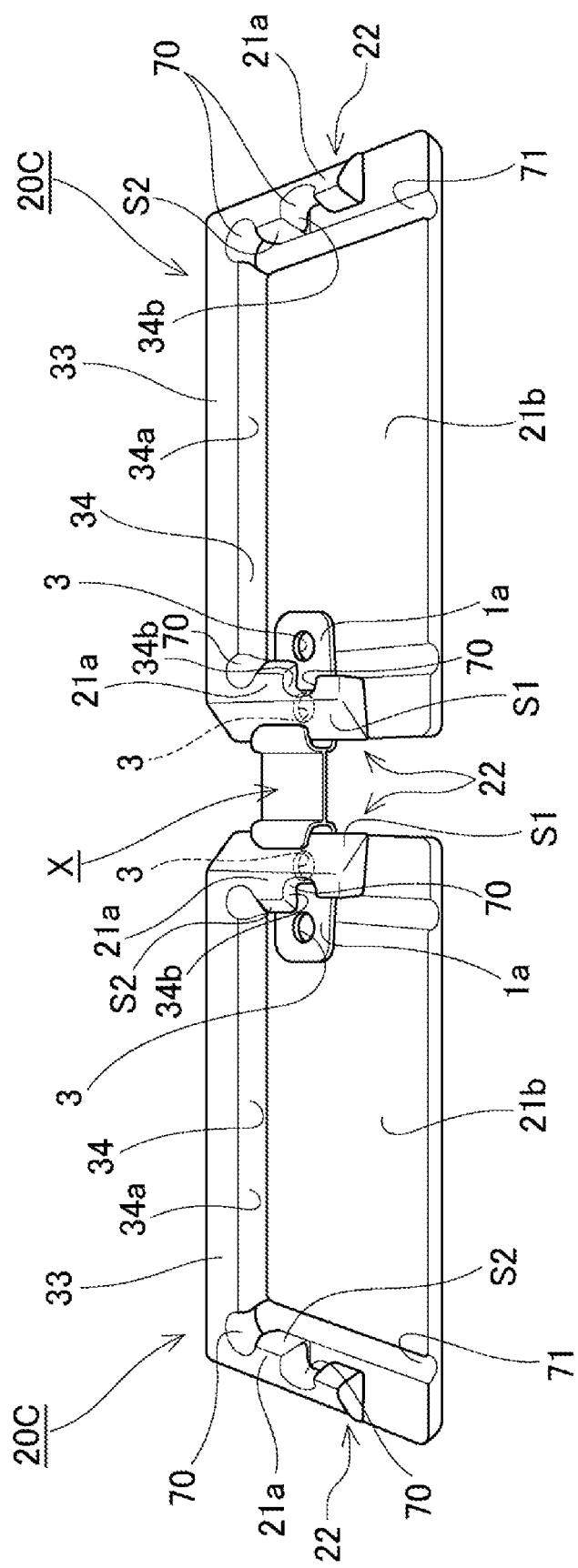
FIG. 11 is a perspective view of a modification of the forming jig given as the third embodiment of the present invention.

The forming jig 20C may be formed, as illustrated in FIG. 11, in a thin and compact shape when formed with a highly rigid material, such as stainless steel.

Figure 12:
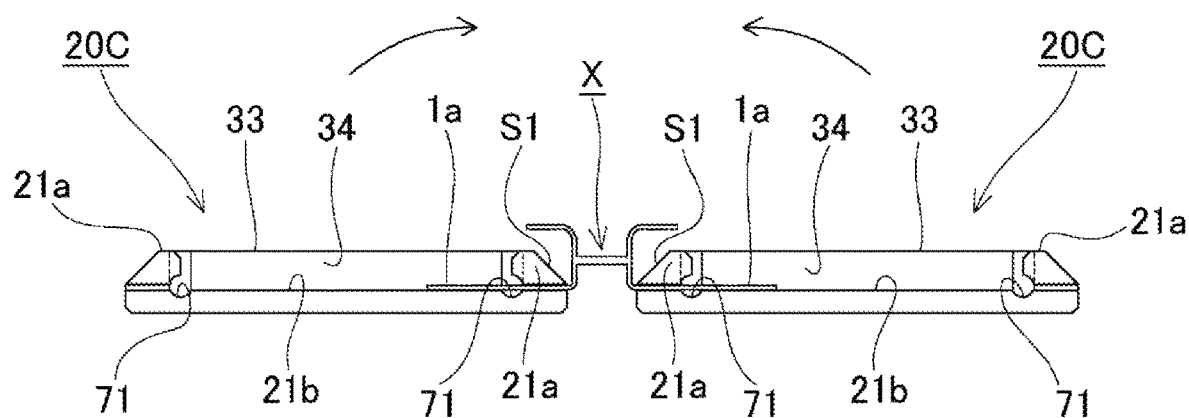
FIG. 12 is a front view of a modification of the forming jig given as the third embodiment of the present invention.

As illustrated in FIG. 11 and FIG. 12, the left and right upper maintaining sections 21a, 21a of the forming jig 20C may be formed with an identical thickness.

In the upper maintaining sections 21a, 21a of the forming jig 20C, when the front piece 1a to be bent is placed to one of the upper maintaining sections 21a, another front piece 1a does not have to be covered with the other upper maintaining section 21a.

The side end surface S2 may have an inclined surface extending in the width direction towards the maintaining surface 31a.

As illustrated in FIG. 11, the upper maintaining section 21a of the forming jig 20C may have a width dimension varied in the longitudinal direction. The upper maintaining section 21a thus formed exhibits the effect of allowing the single forming jig 20C to handle front pieces 1a having different positions of the holes 3 from the base end or positions between the holes 3, 3.

An inside of a corner formed by the linking section 33 and the upper maintaining section 21a (i.e., inner wall side of an intersection of the upper maintaining section 21a and the linking section 33) 70 and a corner 70 to vary the width dimension of the upper maintaining section 21a may be cylindrically notched. In formation of the forming jig 20C, even when a corner where planes meet each other perfectly at a desired angle is intended to be formed, the excess thickness of the forming jig 20C is built up in a very tiny area at the intersection of the corner. In this situation, it is not possible to lay the end of the treatment tool X on the side wall 34a of the storage section 34 to catch the treatment tool X, causing instability. Accordingly, a cylindrical notch 70 is provided as the corner 70 to avoid formation of a corner with the excess thickness built up in the area where planes meet each other and it is thus possible to securely lay the treatment tool X on the side wall 34a. The same applies to the corner 70 to vary the width dimension of the upper maintaining section 21a because a surface 34b facing the direction of the distal end of the upper maintaining section 21a catches a portion of the treatment tool X.

The lower maintaining section 21b may have a front surface along the side end surfaces S2 with linear grooves 71 formed therein. Formation of such grooves 71 reduces a friction surface between the treatment tool X and the lower maintaining section 21b and thus exhibits the effect of allowing prevention of minute flaws and the like in the treatment tool X.

When the front piece 1a is intended to be bent on the base end side with respect to the hole 3 on the base end side of the front piece 1a, as illustrated in FIG. 11 and FIG. 12, the front piece 1a may be sandwiched on both sides using two of the forming jigs 20C for bending in the direction of folding the forming jigs 20C, 20C to each other. Such a bending method is similarly applicable to the forming jig 20C illustrated in FIG. 8.

Figure 13:
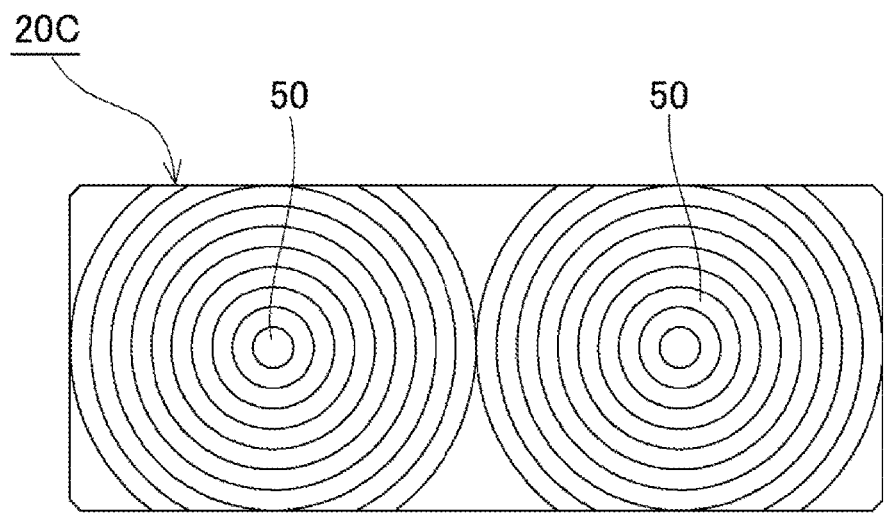
FIG. 13 is a rear view of a modification of the forming jig given as the third embodiment of the present invention.

As illustrated in FIG. 13, the lower maintaining section 21b may have a back surface with a non-slip pattern 50 formed as a concentric wavy uneven surface. In this case, a plurality of such a concentric uneven non-slip pattern 50 may be formed in alignment in a position where the bulbs of the fingers roughly touch when the forming jig 21C is gripped. The non-slip pattern 50 thus formed exhibits the effect of allowing recognition by feeling of the position suitable for gripping of the forming jig 20C. The non-slip pattern 50 is not limited to the shape illustrated in FIG. 13.

Figure 14:
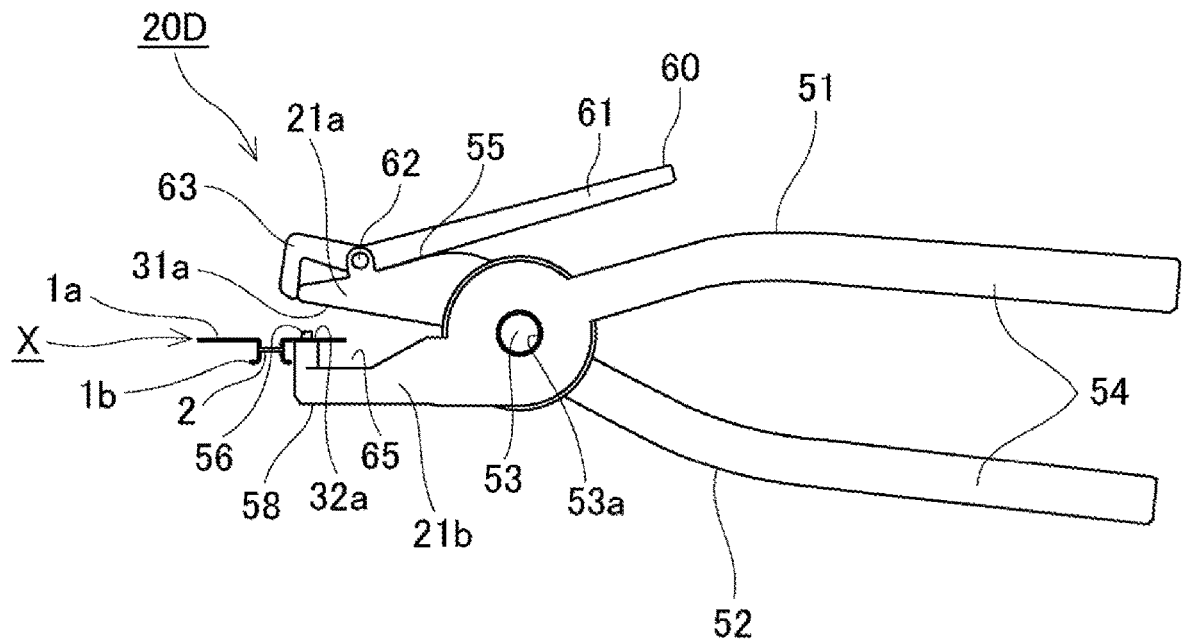
FIG. 14 is a side view illustrating a method for using a forming jig given as a fourth embodiment of the present invention.
Figure 15:
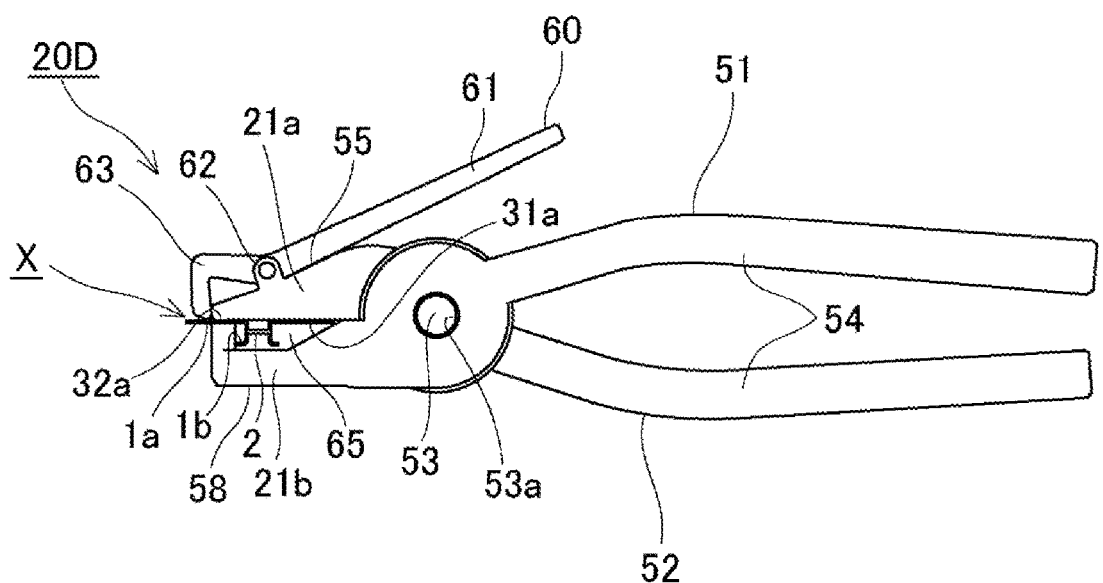
FIG. 15 is a side view illustrating a method for using the forming jig given as the fourth embodiment of the present invention.
Figure 16:
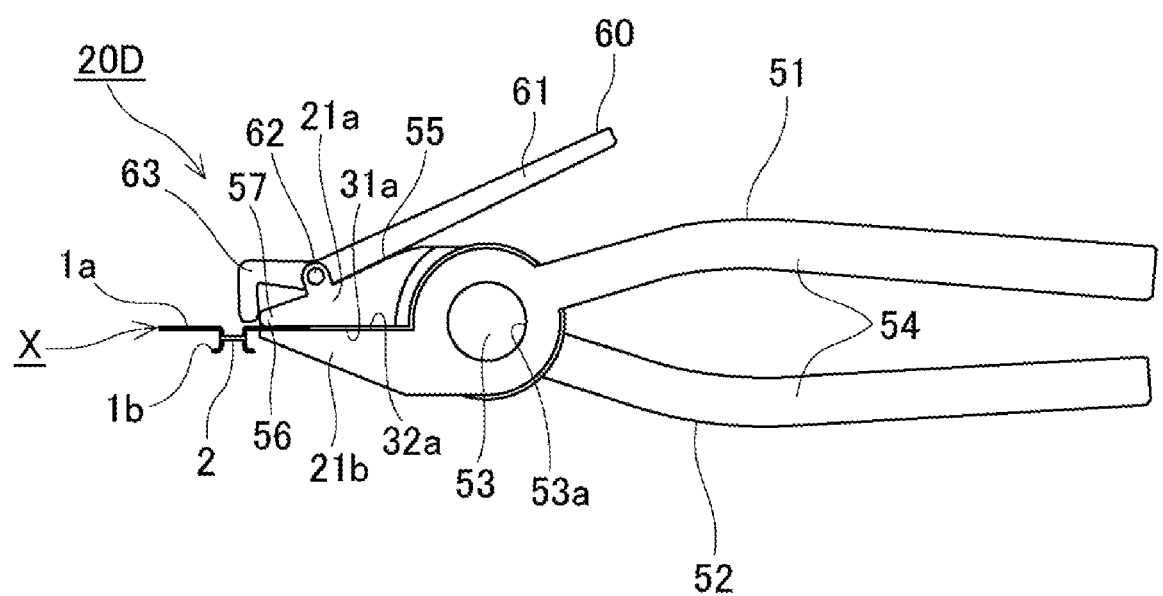
FIG. 16 is a side view illustrating a method for using a modification of the forming jig given as the fourth embodiment of the present invention.

With reference to FIGS. 14-16, a forming jig 20D in the fourth embodiment of the present invention is then described.

The forming jig 20D in the present embodiment is a modification of the forming jig 20A in the first embodiment, and the description in common with the forming jig 20A in the first embodiment is omitted to mainly describe differences.

As illustrated in FIG. 14, the forming jig 20D includes a pair of clamp halves 51, 52 rotatably fixed to a pivot 53.

The clamp half 51 includes: a lower maintaining section 21b formed on a distal end side of an insertion section 53a of the pivot 53; and a lever 54 formed on the opposite side of the lower maintaining section 21b relative to the insertion section 53a.

The clamp half 52 includes: an upper maintaining section 21a formed on the distal end side of the insertion section 53a of the pivot 53; and a lever 54 formed on the opposite side of the upper maintaining section 21a relative to the insertion section 53a.

The clamp halves 51, 52 are assembled by fitting the pivot 53 to the insertion section 53a to cross each other on the pivot 53 as the point of intersection and have a configuration of so-called pliers.

The upper maintaining section 21a and the lower maintaining section 21b form a pair and have maintaining surfaces 31a, 32a capable of sandwiching and fixing the front piece 1a. The maintaining surfaces 31a, 32a are formed at distal ends of the upper maintaining section 21a and the lower maintaining section 21b and have respective flat surfaces to be in tight contact with each other.

The upper maintaining section 21a has an inclined surface (may be referred to as an "outer side wall") 55 extending in a V shape towards the base end, that is, the pivot 53 at a predetermined angle relative to the maintaining surface 31a. The angle between the maintaining surface 31a and the inclined surface 55 is set at, but not necessarily limited to, 10 degrees or more and 30 degrees or less and preferably set at 15 degrees or more and 25 degrees or less.

The lower maintaining section 21b on the base end side with respect to the maintaining surface 32a is notched to form a space 65. The lower maintaining section 21b has an outer side wall 58 formed in a substantially L shape.

The upper maintaining section 21a and the lower maintaining section 21b have a width dimension (depth dimension in FIG. 14) set equal to or more than the width dimension of the front piece 1a.

The maintaining surface 32a as one of the pair has a protrusion 56 to be fit to the hole 3 in the front piece 1a formed thereon, and the other maintaining surface 31a has a depressed area, not shown, formed to receive the protrusion 56. When the protrusion 56 is inserted into the hole 3, the maintaining surfaces 31a, 32a are formed to be capable of covering at least the entire hole 3.

To the inclined surface 55, a pressing member 60 is fixed to bend the front piece 1a projecting from the distal end of the upper maintaining section 21a in the area closest to the distal end of the upper maintaining section 21a.

The pressing member 60 has a lever portion 61, a pivot 62, and a pressing portion 63.

The lever portion 61 is formed in a linear rod shape.

The pressing portion 63 starts from the pivot 62, extends in a direction away from the inclined surface 55, and is bent in a substantially L shape. The pressing portion 63 approaches the inclined surface 55 of the upper maintaining section 21a in cooperation with lifting of the lever portion 61 to press and bend the front piece 1a projecting from the distal end of the upper maintaining section 21a.

When the base end side with respect to the hole 3 on the base end side of the front piece 1a is intended to be bent in the above configuration, as illustrated in FIG. 14, the protrusion 56 is inserted into the hole 3 on the base end side of the front piece 1a and sandwiched by the upper maintaining section 21a and the lower maintaining section 21b to cause the bridging section 2 to project from the distal end. In this case, the forming jig 20D is set to cover the hole 3 on the base end side with the maintaining surfaces 31a, 32a and to locate a distal end edge of the maintaining surface 31a in a position away from the hole 3. Since the distal end of the rear piece 1b of the front piece 1a placed on the maintaining surface 32a comes to a position in substantial contact with the outer side wall 58 of the lower maintaining section 21b, setting of the treatment tool X is facilitated.

After the front piece 1a is sandwiched by the upper maintaining section 21a and the lower maintaining section 21b, the lever 61 is pressed down and the pressing portion 63 presses down the base end side with respect to the hole 3 to bend the front piece 1a.

When an area between the holes 3, 3 in the front piece 1a is intended to be bent, it is also possible to insert the protrusion 56 into the hole 3 on the distal end side of the front piece 1a, and similar to the illustration in FIG. 14, to cause the bridging section 2 to project from the distal ends of the upper maintaining section 21a and the lower maintaining section 21b. In this case as well, it is possible to reliably cover the hole 3, to locate the distal end edge of the maintaining surface 32a between the holes 3, 3, and to bend in the area closest to the distal end edge.

It should be noted that, when only the distal end of the front piece 1a is sandwiched by the upper maintaining section 21a and the lower maintaining section 21b, it is sometimes difficult to set the treatment tool X due to poor balance and it is thus preferred to set as illustrated in FIG. 15 for bending of the holes 3, 3.

That is, the protrusion 56 is inserted into the hole 3 on the base end side of the front piece 1a intended to be bent and the bridging section 2 and the other front piece 1a are contained in the space 65. In this manner, the distal end edge of the maintaining surface 32a is located between the holes 3, 3 in the front piece 1a to allow bending in this area. The treatment tool X thus set causes the distal end of the rear piece 1b to approach the notched inner side wall of the lower maintaining section 21b and it is thus possible to prevent a large tilt of the treatment tool X to the bridging section 2 side and to facilitate placement of the treatment tool X. In addition, the distal end of the other front piece 1a different from the front piece 1a to be bent is supported by the inner side wall of the lower maintaining section 21b, causing an increase in the stability of the treatment tool X while being placed.

In the above configuration, the forming jig 20D exhibits the effect of allowing the front piece 1a to be readily and reliably maintained while covering the hole 3 and the periphery intended to avoid bending and the effect of allowing easy bending of the front piece 1a by the pressing member 60 in an area not through the holes 3.

The configuration of the forming jig 20D exhibits the effect of, when an area between the holes 3, 3 is bent, allowing the distal end of the front piece 1a to project from the upper maintaining section 21a and the lower maintaining section 21b and the other portions to be stably and reliably maintained by the maintaining surfaces 31a, 32a and the space 65.

As illustrated in FIG. 16, the forming jig 20D may be configured to allow tight contact with the maintaining surfaces 31a, 32a without forming a notch constituting the space 65 in the lower maintaining section 21b.

In such configuration as well, the forming jig 20D exhibits the effect of allowing the hole 3 in the front piece 1a to be reliably covered with the upper maintaining section 21a and the lower maintaining section 21b and allowing the front piece 1a projecting from the distal ends of the upper maintaining section 21a and the lower maintaining section 21b to be bent in the area closest to the distal end.

Although some embodiments of the present invention are described above as examples, the present invention is not limited to the contents of these embodiments and the configuration in the respective embodiments may be appropriately applied in combination. For example, such an application is available where the locking member 37 as described in the third embodiment is used for the forming jig 20B in the second embodiment to prevent opening of the clip section 22.

While the methods are described in the above embodiments where only one forming jig of any of 20A-20C is used and another jig, such as pliers, is used for the distal end of the front piece 1a projecting from the clip section 22, the front piece 1a may be bent by maintaining the distal end of the front piece 1a projecting from the clip section 22 with the clip section 22 of still another forming jig of any of 20A-20C. Maintaining of the distal end projecting from the clip section 22 with any of the forming jigs 20A-20C in such a manner exhibits the effect of even more facilitation of bending and allowing prevention of bending of the front piece 1a on a line through the hole 3 formed at the distal end.

REFERENCE SIGNS LIST

1 Clamping Section
1a Front Piece
1b Rear Piece
2 Bridging Section
3 Hole
11 Thyroid Cartilage
20A-20D Forming jig
21 Maintaining Section
21 Upper Maintaining Section
22 Clip Section
25, 56 Protrusion
24a, 24b, 31a, 32a, 32b Maintaining Surface
30B, 30C Operating Section
33 Linking Section (Side Wall)
34 Storage Section
39 Locking Section
45 Recess
53 Pivot
54 Lever (Operating Section)
60 Pressing Member
70 Cylindrical Notch
71 Groove
S End Edge
S1 Inclined Surface
X Dysphonia Treatment Tool

The invention claimed is:

1. An apparatus for forming a dysphonia treatment tool for treating dysphonia by deformation using a forming jig, the apparatus comprising:
   the dysphonia treatment tool comprising:
      a plurality of clamping sections each having a front piece and a rear piece, each clamping section configured to be fit to respective cut ends of incised thyroid cartilage, and the cut ends facing each other, wherein the front piece of the clamping section is configured to be disposed on a front surface of the incised thyroid cartilage, and the rear piece of the clamping section is configured to be disposed on a rear surface of the incised thyroid cartilage, and the front piece has a hole formed therein, and
      a bridging section linking the clamping sections to each other; and
   the forming jig comprising;
      a clip section including a pair of maintaining sections, the maintaining sections configured to sandwich the front piece of the clamping section, partially covering a front surface and a back surface of the front piece of the clamping section to cover at least a portion of the hole of the front piece, wherein an uncovered portion of the front piece of the clamping section projects out from an edge of at least one of the pair of the maintaining sections.

2. The apparatus for forming a dysphonia treatment tool according to claim 1, wherein at least one of the pair of maintaining sections has an inclined surface with a thickness that gradually decreases towards an edge of the maintaining section.

3. The apparatus for forming a dysphonia treatment tool according to claim 1, wherein the pair of maintaining sections includes an upper maintaining section and a lower maintaining section, wherein a space is provided between the upper and lower maintaining sections to receive and partially cover the front piece of the clamping section.

4. The apparatus for forming a dysphonia treatment tool according to claim 1, wherein the pair of maintaining sections includes an upper maintaining section and a lower maintaining section which have surfaces facing each other, wherein one of the pair of maintaining sections has a surface with a linear groove formed along an edge.

5. The apparatus for forming a dysphonia treatment tool according to claim 1, wherein the pair of maintaining sections includes an upper maintaining section and a lower maintaining section,
   wherein the lower maintaining section has a linking section rising from an end along one side at a substantially right angle to form a side wall,
   the side wall intersects with the upper maintaining section, and a substantially cylindrical notch is formed in the inner wall at the intersection of the side wall and the upper maintaining section.

6. The apparatus for forming a dysphonia treatment tool according to claim 1, wherein the pair of maintaining sections includes an upper maintaining section and a lower maintaining section,
   wherein one of the pair of the maintaining sections has a longitudinal direction defined as a direction orthogonal to a space between the upper and lower maintaining sections, and
   a width dimension of this maintaining section varies in the longitudinal direction to allow selection of a dimension which covers the front piece of the clamping section.

7. The apparatus for forming a dysphonia treatment tool according to claim 6, wherein the width dimension of the maintaining section which covers the front piece of the clamping section varies at a corner which is notched substantially cylindrically.

8. The apparatus for forming a dysphonia treatment tool according claim 1, wherein the pair of maintaining sections includes an upper maintaining section and a lower maintaining section,
   wherein the upper and lower maintaining sections has surfaces facing each other, and
   one of the upper surface or the lower surface has a protrusion configured to be inserted into the hole.

9. The apparatus for forming a dysphonia treatment tool according to claim 1, wherein the clip section includes a storage section capable of disposing the bridging section.

10. The apparatus for forming a dysphonia treatment tool according to claim 1, wherein the clip section includes a pressing member to press and bend the front piece of the clamping section sandwiched by the clip section.

11. The apparatus for forming a dysphonia treatment tool according to claim 1, wherein the pair of maintaining sections includes an upper maintaining section and a lower maintaining section,
   wherein the upper and lower maintaining sections have surfaces facing each other each having a recess configured to allow fitting of a portion of the front piece of the clamping section between the facing surfaces.

12. The apparatus for forming a dysphonia treatment tool according to claim 1, further comprising a locking section configured to fix the pair of maintaining sections to each other.

13. The apparatus for forming a dysphonia treatment tool according to claim 1, further comprising an operating section configured to operate the clip section.

14. The apparatus for forming a dysphonia treatment tool according to claim 13, wherein the operating section is a lever cooperating with the pair of maintaining sections formed via a pivot to open and close the pair of maintaining sections.

15. A method for bending a front piece of a dysphonia treatment tool, the dysphonia treatment tool comprising
   a plurality of clamping sections each having
      a flat-plate front piece configured to be disposed on a front surface of incised thyroid cartilage, and
      a rear piece configured to be disposed on a rear surface of the incised thyroid cartilage, the clamping sections being configured to be fit to respective cut ends of the incised thyroid cartilage facing each other,
   the front piece having a hole formed therein, and
   the clamping sections comprising a bridging section linking the clamping sections to each other,
the method comprising:
   sandwiching a portion of the front piece of the clamping section by a clip section including a pair of maintaining sections configured to sandwich the front piece of the clamping section by partially covering a front surface and a back surfaces of the front piece of the clamping section,
      wherein a remaining portion of the front piece of the clamping section projects out from an edge of at least one of the pair of maintaining sections;
   temporarily setting a linear bending line for bending the clamping section at a position which does not overlap the hole in the front piece of the clamping section;
   causing one of the side edges of the maintaining sections to extend along the bending line; and
   holding the remaining portion of the front piece of the clamping section to bend the front piece about the side edge.

\* \* \* \* \*